United States Patent [19]

Chadwick et al.

[11] Patent Number: 5,229,122
[45] Date of Patent: Jul. 20, 1993

[54] PESTICIDAL COMPOSITIONS

[75] Inventors: Peter R. Chadwick; David A. Jeffries, both of Berkhamsted, England

[73] Assignee: Burroughs Wellcome Co., Research Triangle Park, N.C.

[21] Appl. No.: 803,911

[22] Filed: Dec. 9, 1991

Related U.S. Application Data

[60] Continuation of Ser. No. 683,496, Apr. 10, 1991, abandoned, which is a division of Ser. No. 326,466, Mar. 21, 1989, abandoned, which is a continuation of Ser. No. 11,060, Feb. 4, 1987, abandoned.

[30] Foreign Application Priority Data

Feb. 7, 1986 [GB] United Kingdom ............... 8603061

[51] Int. Cl.$^5$ ............................................. A01N 25/28
[52] U.S. Cl. ...................................... 424/408; 424/409
[58] Field of Search ............... 424/429, 405, 408, 409; 514/65, 66, 88, 918, 919

[56] References Cited

U.S. PATENT DOCUMENTS

| 3,074,845 | 1/1963 | Geary | 424/419 |
| 4,670,246 | 8/1987 | Dahl et al. | 424/419 |
| 4,775,534 | 10/1988 | Bartlett et al. | 424/419 |

FOREIGN PATENT DOCUMENTS

| 000827 | 2/1980 | European Pat. Off. | 424/419 |
| 0008207 | 2/1980 | European Pat. Off. | 424/419 |
| 1513614 | 6/1978 | United Kingdom | 424/419 |
| 2027346 | 8/1979 | United Kingdom | 424/417 |
| 2018593 | 10/1979 | United Kingdom | 424/408 |

Primary Examiner—Thurman K. Page
Assistant Examiner—N. Levy
Attorney, Agent, or Firm—Nixon & Vanderhye

[57] ABSTRACT

A microencapsulated pesticide formulation comprises non-encapsulated pesticide as well as encapsulated pesticide. The two pesticides may be the same or different, and typically a formulation of 25% permethrin has 20% permethrin inside the capsules and 5% outside.

2 Claims, No Drawings

PESTICIDAL COMPOSITIONS

This is a continuation of application Ser. No. 07/683,496, filed Apr. 10, 1991, which is a division of Ser. No. 07/326,466, filed Mar. 21, 1989, which is a continuation of Ser. No. 07/011,060, filed Feb. 4, 1987, all abandoned.

This invention relates to pesticidal formulations.

It is known to encapsulate pesticidal compounds in small "microcapsules" of material, to provide a dry flowable formulation and/or to obtain a formulation having a longer effective life. The latter effect is obtained because the microcapsules protect the pesticide from degradation, but themselves slowly degrade, or are broken by applied pressure, to release the pesticide over a period. Alternatively, the pesticide may slowly diffuse through the walls of the microcapsules.

EP 148 769 discloses microcapsule-containing formulations having microcapsules of varying sizes.

It has now been found to be advantageous to include in a formulation comprising microcapsules containing a pesticide the same or another pesticide in a non-encapsulated form.

Accordingly, one aspect of the present invention provides a pesticidal formulation comprising microencapsulated pesticide and non-microencapsulated pesticide.

The terms "microencapsulated" or "microcapsule" are used in this specification to refer to capsules having a diameter of less than 4 mm, particularly less than 2 mm. Commonly, however, microcapsules have an average diameter of between 1 micron and 100 microns.

The microencapsulated pesticide may be the same as or different from the non-encapsulated pesticide. More than one pesticide may be encapsulated, and more than one pesticide may be non-microencapsulated. The encapsulated pesticide(s) may be in one or more than one type of microcapsule.

In relation to the total amount of pesticide in the formulation, the proportion which is non-encapsulated is preferably at least 0.5%, and, in order of increasing preference, at least 1%, 2%, 3%, 4%, 5% and ideally at least 10%. About 15-30%, particularly about 25%, is preferred. Upper limits of 50%, especially 40% and more especially 30%, are particularly preferred, in conjunction with any of the said lower limits.

The microcapsules may be formed by any known means, for example by the so-called "Pennwalt" method described in UK Patent Specification No 1 091 141, the entire contents of which are incorporated herein by reference.

The non-encapsulated material may be a wettable powder, an emulsifiable concentrate, a micro-emulsion, a dust or any other suitable form.

Any known pesticide may be used in the formulation, for example organochlorines such as DDT or lindane, organophosphates such as dursban or chlorpyrifos, formamidines such as amitraz, chitin synthesis and juvenile hormone inhibitors or mimics such as diflubenzuron and methoprene, carbamates such as carbaryl, pyrethroids such as permethrin, deltamethrin, cyhalothrin or cypermethrin, lipid amides ("isobutylamides") and bicyclooctanes.

The total proportion of pesticide in the formulation will depend upon the pesticide(s) in question and the use to which the formulation is being put, but is generally between 0.001 and 90%, typically between 0.01 and 90%, preferably (in the case of permethrin) 10 to 50%, conveniently 20-40%. In the case of other pesticides, these amounts may be varied to suit the potency of the pesticide. For example, deltamethrin or cypermethrin might be used at 1 to 10%, conveniently 2 to 4%. Other excipients known in the art may also be used, for example diluents, carriers, dyes, lubricants, stabilisers, surfactants and, in particular, synergists such as piperonyl butoxide.

Formulations in accordance with the invention may be used against insect and acarine pests and are particularly suitable for coating surfaces such as wood, concrete, brickwood, paint, plaster or metal in order to provide a long-lasting residual action or for use in bait formulations. Surfaces in buildings may be treated to combat crawling insects such as cockroaches or ants, or flying insects, such as houseflies or mosquitoes, when they walk on the treated surface. Stored produce such as grain may also be treated. Animals such as cattle may be treated topically, for example sprayed, to combat biting and nuisance flies and also ticks. Formulations in accordance with the invention may be added to animal feed to combat insect larvae in the animal's dung. If the pesticide is active in the vapour phase, a sustained release of such vapour may be achieved to combat flying insects when they are flying. Crops may be treated with formulations of the inventions, as may stretches of water to kill larvae.

The inclusion of non-encapsulated pesticide provides an immediate dose of such pesticide even before the encapsulated pesticide becomes available, and it has been found that careful control of specific insect populations can be more easily achieved. For example, a large initial dose of pesticide can be used to control, flush out or activate all or almost all of the active adult population of, say, a population of cockroaches, with a continued lower dose from the encapsulated material being provided thereafter to control immigration of adults and emergence of nymphs. Furthermore, two mutually incompatible pesicides may be included in the formulation: a less-stable non-encapsulated one, with a more stable encapsulated one, so that the non-encapsulated one will have been degraded or dispersed by the time that at least the bulk of the encapsulated pesticide emerges. A knock-down agent may be used as the non-encapsulated pesticide, with a kill agent inside the microcapsules.

It has also been found that the presence of the pesticide outside the microcapsule stabilises the pesticide inside the capsule, and the capsule itself, particularly when the pesticides are the same, thus prolonging the active life of the encapsulated material.

Formulations in accordance with the invention may take the form of dry granular matter or aqueous suspensions. Alternatively, a water-soluble wall material may be used in a non-aqueous solvent. The formulations may be packaged in any convenient way, for example in drums or sachets, and would normally be diluted before use. Conveniently, the (optionally diluted) formulation is sprayed onto the surface to be treated, to the point of "run off", by means of compression sprayers, hydraulic sprayers, mist blowers or the like.

The following non-limiting example illustrates a specific embodiment of the invention.

EXAMPLE 1

An oil-in-water encapsulation with a polyurea-polyamide skin represents production of a copolymer (strengthened by cross-linking) by interfacial polycondensation. Charges were prepared as follows:

In flask:
200 ml 0.5% aqueous "Elvanol 50-42" solution

In 1st funnel:
100 ml xylene
15 ml toluene 2,4-diisocyanate
2 ml trimesoyl trichloride (for cross-linking)
120 g permethrin plus 50 ml "Solvesso 200"

In 2nd funnel:
10 g ethylenediamine
5 g diethylenetriamine
10 g sodium carbonate, monohydrate
80 ml distilled water

["Elvanol" (RTM) is a protective colloid comprising polyvinyl alcohol available from DuPont, Wilmington, Del.; "Solvesso 200" is a blend of aromatic hydrocarbons available from Exxon.]

During the addition from the first funnel, which was rapidly effected, the mixture was strongly agitated to form visible droplets, the agitation being slowed down following completion of the first addition. Slow agitation was continued during the second, similarly rapid, addition. Contents were stirred for one hour and then filtered. Capsules of xylene were obtained, containing permethrin.

The microcapsules were mixed with permethrin and "Etocas 29" surfactant (a castor oil derivative available from Croda Chemicals, Goole, UK) in water to give a 25% permethrin dilutable aqueous suspension having 20% permethrin inside the microcapsules and 5% outside.

EXAMPLE 2

The procedure of Example 1 was followed, except that the trimesoyl trichloride was omitted and toluene 2,6-diisocyanate was used 20/80 with the toluene 2,4-diisocyanate to give a total of 15 ml as before. A polyurea wall is thereby formed. To form an emulsifiable concentrate outside the capsules, a blend of 5% permethrin, 2-5% nonylphenol ethylene oxide condensates 2-5% calcium dodecyl benzene sulphonate and about 5% of "Solvesso 200" was made, the percentages, relating to the total formulation when the e.c. is added to the microcapsule preparation.

EXAMPLE 3

The procedure of Example 2 was followed, except that a wettable powder of deltamethrin, a diatomaceous earth and wetters was used as the non-encapsulated part; fenitrothion was used in place of the encapsulated permethrin; and the amount of isocyanate was increased to 25 ml to give a greater wall thickness. The final formulation had a total of 1% deltamethrin outside and 20% fenitrothion inside the microcapsules.

BIOLOGICAL TEST

The formulation of Example 1 was diluted with water 160× and sprayed onto male *Blattella germanica*. The time for knockdown of 50% of the insects ($KT_{50}$) was 6.6 minutes, and all of the insects were dead after day 1.

We claim:

1. A method of controlling insect and acarine pests which crawl, which comprises applying a coating on building surfaces in an amount sufficient to control said pests of a coating composition consisting of 20% to 40% by weight of permethrin, or pyrethroid equivalent of 20% to 40% by weight of permethrin, in both encapsulated and non-encapsulated form, in which the ratio between the non-encapsulated pyrethroid and encapsulated pyrethroid is 0.1 to 0.6.

2. A method of controlling cockroach infestations, which comprises applying to a building surface upon which the cockroach can crawl a coating composition in an amount sufficient to control said pests consisting of 20% to 40% by weight of permethrin, or pyrethroid equivalent of 20% to 40% by weight of permethrin, in both encapsulated and non-encapsulated form, in which the ratio between the non-encapsulated pyrethroid and encapsulated pyrethroid is 0.1 to 0.6.

* * * * *